US009265852B2

(12) United States Patent
Casazza et al.

(10) Patent No.: US 9,265,852 B2
(45) Date of Patent: Feb. 23, 2016

(54) DEORDORISING COMPOSITIONS AND DEODORISING PRODUCTS CONTAINING SAME

(75) Inventors: André Casazza, Grasse (FR); Raymond Kerverdo, Saint Vallier de Thiey (FR); Lydia Ziegler, Grasse (FR); Hugues Brevard, Grasse (FR)

(73) Assignee: ROBERTET S.A., Grasse (FR)

(*) Notice: Subject to any disclaimer, the term of this patent is extended or adjusted under 35 U.S.C. 154(b) by 1091 days.

(21) Appl. No.: 13/379,278

(22) PCT Filed: Jun. 17, 2010

(86) PCT No.: PCT/FR2010/000448
§ 371 (c)(1),
(2), (4) Date: Apr. 27, 2012

(87) PCT Pub. No.: WO2010/146258
PCT Pub. Date: Dec. 23, 2010

(65) Prior Publication Data
US 2012/0201778 A1 Aug. 9, 2012

(30) Foreign Application Priority Data
Jun. 18, 2009 (FR) .................................... 09 07987

(51) Int. Cl.
A61L 9/00 (2006.01)
A61L 9/01 (2006.01)

(52) U.S. Cl.
CPC ...................... A61L 9/01 (2013.01)

(58) Field of Classification Search
CPC ........................................................ A61L 9/01
See application file for complete search history.

(56) References Cited

U.S. PATENT DOCUMENTS

| 3,325,367 | A |   | 6/1967  | Roberta              |          |
|-----------|---|---|---------|----------------------|----------|
| 3,852,355 | A |   | 12/1974 | Rautenstrauch et al. |          |
| 3,944,621 | A |   | 3/1976  | Mookherjee et al.    |          |
| 5,795,566 | A | * | 8/1998  | Joulain et al.       | 424/76.1 |
| 5,968,795 | A |   | 10/1999 | Dixon et al.         |          |

FOREIGN PATENT DOCUMENTS

| DE | 4417752 A1       | 11/1995 |
| EP | 1224947 A1       | 7/2002  |
| JP | 61-53238 A       | 3/1986  |
| NL | 8104274 A        | 4/1983  |
| WO | WO 2006076821 A1 | 7/2006  |
| WO | WO 2008149102 A2 | 12/2008 |

OTHER PUBLICATIONS

Translation of NL8104274A, Feb. 2015.*

(Continued)

Primary Examiner — Paul Dickinson
(74) Attorney, Agent, or Firm — Browdy and Neimark, P.L.L.C.

(57) ABSTRACT

The invention relates to novel deodorant compositions containing at least one compound of the family of acetylenic ketones and the deodorant products containing them. A particularly preferred composition according to the invention comprises at least one compound of the family of the α-acetylenic ketones and a mixture of aldehydes chosen from two different families.

18 Claims, 1 Drawing Sheet

(56) References Cited

OTHER PUBLICATIONS

Amaike, et al., "Alkynl-ketone(s) prepn. for fragrance intermediate-by reacting 1-alkyne with acid halogen in presence of acid halogen catalyst, useful for flavanol intermediate", Thomson Scientific, Jul. 24, 1991, 2 pages.

El-Sayed, et al., "Studies of nitrification inhibition with many acetylenic compounds in soils", Alexandria Science Exchange, 2003, 1 page, vol. 24, No. 3.

Roe, et al., "A novel geminal diol as a highly specific and stable in vivo inhibitor of insect juvenile hormone esterase", Archives of Insect Biochemistry and Physiology, 1997, 1 page, vol. 36, No. 3.

Glazunova, et al., "Antimicrobial activity of acetylene keto ethers", Khimiko-Farmatsevticheski Zhurnal, 1974, 4 pages, vol. 8, No. 4.

Yamada, et al., "Characteristic of Artemisia capillaris extract and development with", Fragrance Journal, 2006, 1 page, vol. 34, No. 4.

Gavrilov, et al., "Synthesis of diarylpropynones and their antibiotic activity", Khimiko-Farmatsevticheski Zhurnal, 1978, 4 pages, vol. 12, No. 9.

Oshima, et al., "Capillin-containing odorless antibacterial and antifungal agents, and their compositions", Jpn. Kokai Tokkyo Koho, 2003, 5 pages.

"Acetylene derivatives as nematocides", Jpn. Kokai Tokkyo Koho, 1982, 2 pages.

"Soil disindectant composition", Jpn. Kokai Tokkyo Koho, 1982, 2 pages.

Hillers, et al., "Antibiotic activity of some acetylene derivatives of furan", Latvijas PSR Zinatnu Akademijas Vestis, 1967, 2 pages.

Hillers, et al., "Fungistatic and bacteriostatic activity of some acetylenic derivatives of pathogenic fungi", Khim Atsetilena, 1969, 2 pages.

Katsuta, "Preservation of wood", Jpn. Kokai Tokkyo Koho, 1986, 1 page.

Katsuta, :Pyrethrin insecticides, Jpn. Kokai Tokkyo Koho, 1974, 1 page.

Kawanami, et al., Perfume contg. formyl acetylene derivs with terminal double bond-prepd. from alkane-alpha, omega-di:halide, Thomson Scientific, 1986, 1 page.

\* cited by examiner

DEORDORISING COMPOSITIONS AND DEODORISING PRODUCTS CONTAINING SAME

The present Application relates to novel deodorant compositions containing at least one compound of the family of acetylenic ketones and the deodorant products containing them.

Combating unpleasant odours has led to the use of numerous widely varying substances, for example phenolic substances, essential oils, resins, aldehydes or ketones, alcohol derivatives, esters or others.

Various aldehydes have in particular been used, alone or mixed with numerous other products. Although satisfactory, these products do not always have the desired effectiveness.

A need therefore still exists for more effective deodorant compositions, optionally with a pleasant smell.

After lengthy work, the Applicant has discovered that molecules of the family of acetylenic ketones can be used in deodorant compositions, particularly due to their property of destroying malodorous molecules. It is therefore understood that in the present text the use of the expression "deodorant composition" refers to a composition the deodorant effect of which is linked to the properties of physical destruction of the malodorous molecules by the acetylenic ketones and not to any masking of the unpleasant odour.

In the remainder of the present text, the expression "acetylenic ketone" is used to denote chemical molecules comprising at least one keto-α-acetylenic chain formation (—CO—C≡C— or —C≡C—CO—).

Thus the first subject of the invention is a deodorant composition characterized in that it comprises at least one compound of the family of the α-acetylenic ketones corresponding to general formula 1

$$R-(CO)_k-C\equiv C-(A)-(C\equiv C)_m-(CO)_n-R_1 \quad (1)$$

in which
R and $R_1$ can represent, independently or simultaneously, a radical chosen from
  an alkyl chain comprising from 1 to 9, preferentially from 3 to 7 carbon atoms, linear or branched, substituted or unsubstituted, or
  a cycloalkane comprising from 3 to 8, preferentially 5 or 6 carbon atoms, substituted or unsubstituted; or
  a furan ring, saturated or unsaturated, substituted or unsubstituted; or
  a pyran ring, saturated or unsaturated, substituted or unsubstituted; or
  an aromatic ring comprising from 6 to 8 carbon atoms, substituted or unsubstituted; or also
  a hydrogen atom.
A represents a group chosen from —$(CH_2)_x$— with x representing an integer with a value from 0 to 6, preferentially from 0 to 4, (—CO)$_l$ with l representing an integer with a value of 0 or 1, or also a —$(CH_2)_y$—O—$(CH_2)_z$— chain formation with y and z representing, simultaneously or independently, an integer with a value from 0 to 6, preferentially from 0 to 4, it being understood that x+y does not exceed the value of 6;
k, m and n are, simultaneously or independently, an integer with a value of 0 or 1, it being understood that k and n cannot simultaneously have a value of 0 if l is equal to 0.
with the exception of 2-methyl-4-nonyn-3-one of formula $C_4H_9$—C≡C—CO—CH(CH$_3$)$_2$.

According to the invention, by alkyl chain comprising from 1 to 9 carbon atoms is meant a methyl, ethyl, propyl, butyl, pentyl, hexyl, heptyl, octyl, nonyl radical, linear or branched, substituted or unsubstituted, in particular by one or more oxo group(s), however without the total carbon atoms in the molecule exceeding 18, preferentially 16.

Also according to the invention, by a cycloalkane comprising from 3 to 8 carbon atoms is meant a cyclopropyl, cyclobutyl, cyclopentyl, cyclohexyl, cycloheptyl, cyclooctyl, cyclopropylcarbonyl, cyclobutylcarbonyl, cyclopropylmethyl or also cyclobutylmethyl radical.

Also according to the invention, by an aromatic ring comprising from 6 to 8 carbon atoms is meant a radical chosen from phenyl, benzyl or phenethyl, optionally substituted by one or two substituents, identical or different, chosen from the methyl, dimethyl, methoxy, dimethoxy, hydroxy, acetyl, cyano substituents.

According to the invention, the R and $R_1$ radicals can be simultaneously or independently substituted by one or more radicals chosen from the methyl, ethyl, propyl, butyl radicals or also a 2-oxopropyl radical.

Advantageously according to the invention, R and R1 can be preferentially an acetonyl, pentyl, hexyl, heptyl, cyclopropyl, cyclopentyl, cyclohexyl, furyl or phenyl, anisyl, dimethoxyphenyl, tolyl radical and $R_1$ can be a hydrogen atom.

According to the invention, the compound of formula 1 can be present in the composition in a quantity comprised between 0.01% and 40%, preferentially between 0.1% and 15%, even more preferentially from 1% to 10% of the total weight of the composition.

According to the invention, the composition can comprise one or more compounds corresponding to formula 1.

According to the invention, it is possible to use preferentially in the compositions at least one of the compounds chosen from:
1-octyn-3-one of formula $C_5H_{11}$—CO—C≡CH;
3-octyn-2-one of formula $C_4H_9$—C≡C—CO—CH$_3$;
4-octyn 3-one of formula $C_3H_7$—C≡C—CO—C$_2$H$_5$;
4-nonyn-3-one of formula $C_3H_7$—CH$_2$—C≡C—CO—C$_2$H$_5$;
2-nonyn-4-one of formula CH$_3$—C≡C—CO—C$_5$H$_{11}$;
5-nonyn-4-one of formula $C_3H_7$—CO—C≡C—CH$_2$—C$_2$H$_5$;
1-decyn-3-one of formula $C_7H_{15}$—CO—C≡CH;
4-decyn-3-one of formula $C_5H_{11}$—C≡C—CO—C$_2$H$_5$;
6-decyn-5-one of formula $C_3H_7$—C≡C—CO—C$_4$H$_9$;
5-decyn-4-one of formula $C_4H_9$—C≡C—CO—C$_3$H$_7$;
2-decen-5-yn-4-one of formula $C_4H_9$—C≡C—CO—CH=CH—CH$_3$;
1-(p-methoxyphenyl)-2-propyn-1-one of formula H$_3$C—O—C$_6$H$_4$—CO—C≡CH;
1-cyclopropyl-2-heptyn-1-one of formula $C_4H_9$—C≡C—CO—C$_3$H$_5$ cyclopropyl);
2-methyl-5-decyn-4-one of formula $C_4H_9$—C≡C—CO—CH$_2$—CH(CH$_3$)$_2$;
9-methyl-5-decyn-4-one of formula $C_3H_7$—CO—C≡C—CH$_2$—CH$_2$—CH(CH$_3$)$_2$;
2-methyl-4-octyn-3-one of formula $C_3H_7$—C≡C—CO—CH(CH$_3$)$_2$;
1-phenyl-2-propyn-1-one of formula $C_6H_5$—CO—C≡CH;
4-phenyl-3-butyn-2-one of formula $C_6H_5$—C≡C—CO—CH$_3$;
5-phenyl-4-pentyn-3-one of formula $C_6H_5$—C≡C—CO—C$_2$H$_5$;
6-phenyl-5-hexyn-2,4-dione of formula $C_6H_5$—C≡C—CO—CH$_2$—CO—CH$_3$;
1-phenyl-1-heptyn-3-one of formula $C_6H_5$—C≡C—CO—C$_4$H$_9$;

1-(2-furyl)-3-phenyl-2-propyn-1-one of formula $C_6H_5$—$C\equiv C$—$CO$—$C_4H_3O$ furyl);
1-(2-furyl)-2-octyn-1-one of formula $C_5H_{11}$—$C\equiv C$—$CO$—$C_4H_3O$ (furyl);
$C_6H_5$—$C\equiv C$—$CO$—$C_4H_3O$ (furyl);
3-cyclopropyl-1-(p-tolyl)-2-propyn-1-one of formula $C_3H_2$—$C\equiv C$—$CO$—$C_6H_4$—$CH_3$;
1-cyclopropyl-4-methyl-1-hexyn-3-one of formula $C_3H_5$—$C\equiv C$—$CO$—$CH(C_2H_5)$—$CH_3$ (cyclopropyl);
9-hexadecyn-8-one of formula $C_6H_{13}$—$C\equiv C$—$CO$—$C_7H_{15}$;
5-ethyl-11-methyl-7-dodecyn-6-one of formula $(CH_3)_2CH$—$C_2H_4$—$C\equiv C$—$CO$—$CH(C_2H_5)$—$C_4H_9$;
7-tetradecyn-6-one of formula $C_6H_{13}$—$C\equiv C$—$CO$—$C_5H_{11}$;
1-cyclohexyl-4-ethyl-1-hexyn-3-one of formula $C_6H_{11}$—$C\equiv C$—$CO$—$CH(C_2H_5)_2$ (cyclohexyl);
1-cyclopentyl-4-nonyn-3-one of formula $C_4H_9$—$C\equiv C$—$CO$—$C_2H_4$—$C_5H_9$ (cyclopentyl);
1-cyclohexyl-2-heptyn-1-one of formula $C_4H_9$—$C\equiv C$—$CO$—$C_6H_{11}$ (cyclohexyl);
1-(p-tolyl)-2-butyn-1-one of formula $CH_3$—$C\equiv C$—$CO$—$C_6H_4$-(p-$CH_3$);
2,2,8-trimethyl-4-nonyn-3-one of formula $(CH_3)_2CH$—$C_2H_4$—$C\equiv C$—$CO$—$C(CH_3)_3$;
2,2-dimethyl-4-hexyn-3-one of formula $CH_3$—$C\equiv C$—$CO$—$C(CH_3)_3$;
1,4-diphenyl-2-butyn-1,4-dione of formula $C_6H_5$—$CO$—$C\equiv C$—$CO$—$C_6H_5$;
5-decyn-2,4-dione of formula $C_4H_9$—$C\equiv C$—$CO$—$CH_2$—$CO$—$CH_3$;
1-(3,4-dimethoxyphenyl)-2-butyn-1-one of formula $CH_3$—$C\equiv C$—$CO$—$C_6H_3$—$(OCH_3)_2$;
2,5-heptadiyn-4-one of formula $H_3C$—$C\equiv C$—$CO$—$C\equiv C$—$CH_3$;
3-hexyn-2,5-dione of formula $CH_3$—$CO$—$C\equiv C$—$CO$—$CH_3$;
4-octyn-3,6-dione of formula $C_2H_5$—$CO$—$C\equiv C$—$CO$—$C_2H_5$;
2,7-dimethyl-4-octyn-3,6-dione of formula $(CH_3)_2CH$—$CO$—$C\equiv C$—$CO$—$CH(CH_3)_2$;
2,7-dimethyl-4-octyn-3-one of formula $(CH_3)_2CH$—$CH_2$—$C\equiv C$—$CO$—$CH(CH_3)_2$;
4,7-undecadiyn-6-one of formula $C_3H_7$—$C\equiv C$—$CO$—$C\equiv C$—$C_3H_7$;
5-decyn-4,7-dione of formula $C_3H_7$—$CO$—$C\equiv C$—$CO$—$C_3H_7$;
2,9-dimethyl-5-decyn-4,7-dione of formula $(CH_3)_2CH$—$CH_2$—$CO$—$C\equiv C$—$CO$—$CH_2$—$CH(CH_3)_2$;
6-dodecyn-5,8-dione of formula $C_4H_9$—$CO$—$C\equiv C$—$CO$—$C_4H_9$;
2,11-dimethyl-6-dodecyn-5,8-dione of formula $(CH_3)_2CH$—$C_2H_4$—$CO$—$C\equiv C$—$CO$—$(CH_2)_2$—$CH(CH_3)$;
2,9-dimethyl-5-decyn-4-one of formula $(CH_3)_2CH$—$C_2H_4$—$C\equiv C$—$CO$—$CH_2$—$CH(CH_3)_2$;
7-tetradecyn-6,9-dione of formula $C_5H_{11}$—$CO$—$C\equiv C$—$CO$—$C_5H_{11}$;
4,10-undecadiyn-3-one of formula $HC\equiv C$—$C_4H_8$—$C\equiv C$—$CO$—$C_2H_5$;
2,12-dimethyl-7-oxa-4,9-tridecadiyn-3,11-dione of formula $(CH_3)_2$—$CO$—$C\equiv C$—$CH_2$—$O$—$CH_2$—$C\equiv C$—$CO$—$CH(CH_3)_2$, or also
4,10-tetradecadiyn-3,12-dione of formula $C_2H_5$—$CO$—$C\equiv C$—$C_4H_8$—$C\equiv C$—$CO$—$C_2H_5$.
Very preferentially it is possible to use at least one compound chosen from
1-phenyl-2-propyn-1-one of formula $C_6H_5$—$CO$—$C\equiv CH$;
1-decyn-3-one of formula $C_7H_{15}$—$CO$—$C\equiv CH$;
1-(2-furyl)-2-octyn-1-one of formula $C_5H_{11}$—$C\equiv C$—$CO$—$C_4H_3O$ (furyl);
1-(2-furyl)-3-phenyl-2-propyn-1-one of formula $C_6H_5$—$C\equiv C$—$CO$—$C_4H_3O$ (furyl);
1-octyn-3-one of formula $C_5H_{11}$—$CO$—$C\equiv CH$;
1-(p-tolyl)-2-butyn-1-one of formula $CH_3$—$C\equiv C$—$CO$—$C_6H_4$-(p-$CH_3$);
2,5-heptadiyn-4-one of formula $CH_3$—$C\equiv C$—$CO$—$C\equiv C$—$CH_3$;
1-(p-methoxyphenyl)-2-propyn-1-one of formula $CH_3O$—$C_6H_4$—$CO$—$C\equiv CH$;
1,4-diphenyl-2-butyn-1,4-dione of formula $C_6H_5$—$CO$—$C\equiv C$—$CO$—$C_6H_5$; or also
4,7-undecadiyn-6-one of formula $C_3H_7$—$C\equiv C$—$CO$—$C\equiv C$—$C_3H_7$.

According to a variant of the invention, it is possible to use in the compositions any combination of at least 2 of the compounds corresponding to formula 1, preferentially those previously listed and even more preferentially the pairs formed by 2 compounds chosen from the pairs:
1-phenyl-2-propyn-1-one/1-decyn-3-one;
1-(2-furyl)-2-octyn-1-one/1-decyn-3-one;
1-(2-furyl)-3-phenyl-2-propyn-1-one/1-decyn-3-one;
1-octyn-3-one/1-decyn-3-one;
1-(p-tolyl)-2-butyn-1-one/1-decyn-3-one;
2,5-heptadiyn-4-one/1-decyn-3-one;
1-(p-methoxyphenyl)-2-propyn-1-one/1-decyn-3-one;
1,4-diphenyl-2-butyn-1,4-dione/1-decyn-3-one;
4,7-undecadiyn-6-one/1-decyn-3-one;
1-(2-furyl)-2-octyn-1-one/1-phenyl-2-propyn-1-one;
1-(2-furyl)-3-phenyl-2-propyn-1-one/1-phenyl-2-propyn-1-one;
1-octyn-3-one/1-phenyl-2-propyn-1-one;
1-(p-tolyl)-2-butyn-1-one/1-phenyl-2-propyn-1-one;
2,5-heptadiyn-4-one/1-phenyl-2-propyn-1-one;
1-(p-methoxyphenyl)-2-propyn-1-one/1-phenyl-2-propyn-1-one;
1,4-diphenyl-2-butyn-1,4-dione/1-phenyl-2-propyn-1-one;
4,7-undecadiyn-6-one/1-phenyl-2-propyn-1-one;
1-(2-furyl)-3-phenyl-2-propyn-1-one/1-(2-furyl)-2-octyn-1-one;
1-octyn-3-one/1-(2-furyl)-2-octyn-1-one 1-(p-tolyl)-2-butyn-1-one;
2,5-heptadiyn-4-one/1-(2-furyl)-2-octyn-1-one;
1-(p-methoxyphenyl)-2-propyn-1-one/1-(2-furyl)-2-octyn-1-one;
1,4-diphenyl-2-butyn-1,4-dione/1-(2-furyl)-2-octyn-1-one;
4,7-undecadiyn-6-one/1-(2-furyl)-2-octyn-1-one;
1-octyn-3-one/1-(2-furyl)-3-phenyl-2-propyn-1-one;
1-(p-tolyl)-2-butyn-1-one/1-(2-furyl)-3-phenyl-2-propyn-1-one;
2,5-heptadiyn-4-one/1-(2-furyl)-3-phenyl-2-propyn-1-one;
1-(p-methoxyphenyl)-2-propyn-1-one/1-(2-furyl)-3-phenyl-2-propyn-1-one;
1,4-diphenyl-2-butyn-1,4-dione/1-(2-furyl)-3-phenyl-2-propyn-1-one;
4,7-undecadiyn-6-one/1-(2-furyl)-3-phenyl-2-propyn-1-one;
1-(p-tolyl)-2-butyn-1-one/1-octyn-3-one;
2,5-heptadiyn-4-one/1-octyn-3-one;
1-(p-methoxyphenyl)-2-propyn-1-one/1-octyn-3-one;
1,4-diphenyl-2-butyn-1,4-dione/1-octyn-3-one;
4,7-undecadiyn-6-one/1-octyn-3-one;
2,5-heptadiyn-4-one/1-(p-tolyl)-2-butyn-1-one;
1-(p-methoxyphenyl)-2-propyn-1-one/1-(p-tolyl)-2-butyn-1-one;

1,4-diphenyl-2-butyn-1,4-dione/1-(p-tolyl)-2-butyn-1-one;
4,7-undecadiyn-6-one/1-(p-tolyl)-2-butyn-1-one;
1-(p-methoxyphenyl)-2-propyn-1-one/2,5-heptadiyn-4-one;
1,4-diphenyl-2-butyn-1,4-dione/2,5-heptadiyn-4-one;
4,7-undecadiyn-6-one/2,5-heptadiyn-4-one;
1,4-diphenyl-2-butyn-1,4-dione/1-(p-methoxyphenyl)-2-propyn-1-one;
4,7-undecadiyn-6-one/1-(p-methoxyphenyl)-2-propyn-1-one;
4,7-undecadiyn-6-one/1,4-diphenyl-2-butyn-1,4-dione.

According to the invention, the compound of formula 1 can be present in the composition in a quantity comprised between 0.1% and 40%, preferentially between 0.1% and 10%, of the total weight of the composition.

The compounds of formula 1 are known for their significant reactivity with the thiols and the amines.

They are easily obtained by the usual chemical synthesis routes and particularly
either by the action of an acid chloride on a sodium derivative of an alkyne according to

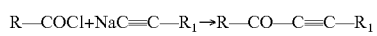
R—COCl+NaC≡C—R₁→R—CO—C≡C—R₁ or by oxidation of a secondary alcohol precursor according to

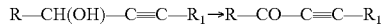
R—CH(OH)—C≡C—R₁→R—CO—C≡C—R₁ or by direct oxidation of an alkyne according to

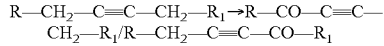
R—CH₂—C≡C—CH₂—R₁→R—CO—C≡C—CH₂—R₁/R—CH₂—C≡C—CO—R₁

According to a variant of the invention, the deodorant composition can moreover comprise at least one aldehyde chosen from the acyclic and non-terpenic aliphatic aldehydes, the non-terpenic alicyclic aldehydes, the terpenic aldehydes, the aliphatic aldehydes substituted by an aromatic group, the bifunctional aldehydes, the aldehydes possessing a non-aromatic unsaturation borne by the carbon in the alpha position of the aldehyde function, the aldehydes possessing an unsaturation in the alpha position of the aldehyde function conjugated with an aromatic ring and the aldehydes the function of which is borne by an aromatic ring. In this variant, the composition can comprise a mixture of two or more aldehydes.

According to another, preferred, variant of the invention, the deodorant composition can moreover comprise a mixture of at least one first aldehyde (aldehyde of class A) chosen from the acyclic and non-terpenic aliphatic aldehydes, the non-terpenic alicyclic aldehydes, the terpenic aldehydes, the aliphatic aldehydes substituted by an aromatic group and the bifunctional aldehydes and at least one second aldehyde (aldehyde of class B) chosen from the aldehydes possessing a non-aromatic unsaturation borne by the carbon in the alpha position of the aldehyde function, the aldehydes possessing an unsaturation in the alpha position of the aldehyde function conjugated with an aromatic ring and the aldehydes the function of which is borne by an aromatic ring. In this variant, the composition can comprise a mixture of at least one first and at least one second aldehyde. But the first aldehyde can of course be a mixture of two or more aldehydes of class A and the second aldehyde can be a mixture of two or more aldehydes chosen from those of class B.

According to the invention, the aldehydes of class A or B can be chosen from the natural or synthetic aldehydes, particularly from those classes which are not dangerous to the environment according to the European Dangerous Substances Directive, authorized in food (FEMA No.) and in perfumery by the IFRA.

According to the invention, the acyclic and non-terpenic aliphatic aldehyde of class A can be chosen from
decanal;
undecanal;
dodecanal;
10-undecenal;
2-methyl undecanal;
trimethyl-2,6,10-undecen-9-al (ADOXAL™); or also
tetramethyl-2,3,5,5-hexanal.

Also according to the invention, the non-terpenic alicyclic aldehyde of class A can be chosen from
2,4-dimethylcyclohex-3-en-1-carboxaldehyde,
1,2-dimethylcyclohex-3-en-1-carboxaldehyde,
3,5-dimethylcyclohex-3-en-1-carboxaldehyde,
2,4,6-trimethylcyclohex-3-en-1-carboxaldehyde (ISOCYCLOCITRAL™),
tricyclo[5.2.1.0(0.6)]decyliden-8)-4-butanal (DUPICAL™);
trimethyl-2,6,10-undecen-9 al (ADOXAL™);
(methyl-4-penten-3-yl)-4-cyclohex-3-en-3-yl-1-carboxaldehyde;
6-methyl-8-(1-methylethyl)bicyclo[2.2.2]-5-octen-2-carboxaldehyde (MACEAL™); or also
8,8-dimethyl-2,3,4,5,6,7-hexahydro-1H-naphthalene-2-carboxaldehyde (ALDEHYDE 111™);
5-methyl furfural;
1-methyl-4-(4-methylpentyl)cyclohex-3-en-1-carboxaldehyde;
3-(5-methyl-2-furyl)butanal,6,6-dimethylbicyclo[3.1.1]-2-heptenyl-2-propanal;
tricyclodecanylcarboxaldehyde; or also
butylcinnamaldehyde Preferentially the non-terpenic alicyclic aldehyde (AliNT) of class A can be chosen from
8,8-dimethyl-2,3,4,5,6,7-hexahydro-1H-naphthalene-2 carboxaldehyde (ALDEHYDE 111™);
5-methyl furfural;
1-methyl-4-(4-methylpentyl)cyclohex-3-en-1-carboxaldehyde;
3-(5-methyl-2-furyl)butanal,6,6-dimethylbicyclo[3.1.1]-2-heptenyl-2-propanal;
tricyclodecanylcarboxaldehyde; or also
butylcinnamaldehyde.

Also according to the invention, the terpenic aldehyde (Terp) of class A can be chosen from
citronellal;
hydroxycitronnellal;
2,2,3-trimethyl-3-cyclopenten-1-acetaldehyde (α-campholenaldehyde);
p-menth-1-en-9-al (carvomenthenal);
7,7-dimethylbicyclo[3.1.1]hept-3-en-4-carboxaldehyde (myrtenal); or also
2-isopropyl-5-methyl-2-hexenal (isodihydrolavandulal).
Preferentially according to the invention, the terpenic aldehyde can be chosen from
α-campholenaldehyde;
carvomenthenal;
myrtenal; or also
isodihydrolavandulal.

Also according to the invention, the aliphatic aldehyde of class A substituted by an aromatic group can be chosen from
2-methyl-3-(p-isopropylphenyl)propanal;
3-(4-tert-butylphenyl)butanal;
phenylacetaldehyde;
3-phenylpropanal;
2-phenylpropanal;
2-methyl-3-(p-methylphenyl)propanal;
Helional™;

cyclamen aldehyde;
lilial;
Canthoxal™; or also
phenylacetaldehyde.

Preferentially according to the invention, the aliphatic aldehyde substituted by an aromatic group can be chosen from
2-methyl-3-(p-isopropylphenyl)propanal;
3-(4-tert-butylphenyl)butanal;
phenylacetaldehyde;
3-phenylpropanal;
2-phenylpropanal; or also
2-methyl-3-(p-methylphenyl)propanal.

By "bifunctional aldehyde", is meant according to the invention the aldehydes also possessing another function such as for example an ether-oxide or alcohol function. The bifunctional aldehyde can according to the invention be chosen from
the alkoxy-acetaldehydes;
the hydroxy-aldehydes;
the alkoxy-aldehydes;
such as for example
3 and 4-(4-hydroxy-4-methylpentyl)-3-cyclohexen-1-carboxaldehyde (LYRAL™);
methoxydicyclopentadiencarboxaldehyde;
3-(1,3-benzodioxol-5-yl)-2-methylpropanal; or also
7-hydroxy-3,7-dimethyloctanal (hydroxycitronellal).

Preferentially according to the invention, the bifunctional aldehyde can be
methoxydicyclopentadiencarboxaldehyde; or also
7-hydroxy-3,7-dimethyloctanal.

According to the invention, the aldehyde which possesses an unsaturation of non-aromatic type (class B) borne by the carbon in the alpha position of the aldehyde function can be chosen from
citral (neral and geranial);
myrtenal;
perillaldehyde;
furyl-2-carboxaldehydes substituted or unsubstituted, preferentially those unsubstituted or substituted by at least one methyl;
2,4-heptadienal;
2E,4E-undecadienal;
2E,4E-dodecadienal;
2E-decenal;
2E,4Z,7Z-tridecatrienal;
2E,6Z-nonadienal;
2-furfurylidenebutanal;
3,7-dimethyl-2-methylen-6-octenal; or also
2E-dodecenal.

Preferentially according to the invention, the aldehyde which possesses an unsaturation of non-aromatic type (class B) borne by the carbon in the alpha position of the aldehyde function can be
citral;
myrtenal;
perillaldehyde;
2E-dodecenal; or also
2-furfurylidenebutanal.

The aldehyde (of class B) which possesses an ethylenic unsaturation in the alpha position, conjugated with an aromatic ring can be chosen from
cinnamaldhyde;
α-amylcinnamaldehyde (JASMONAL™);
α-hexylcinnamaldehyde;
(E)-3-(2-methoxyphenyl)prop-2-enal;
(E)-3-(4-methoxyphenyl)prop-2-enal;
α-methylcinnamaldehyde;
1-benzofuran-2-carboxaldehyde;
2-phenyl-2-butenal; or also
5-methyl-2-phenyl-2-hexenal.

Preferentially according to the invention, the aldehyde which possesses an ethylenic unsaturation in the alpha position, conjugated with an aromatic ring can be
(E)-3-(2-methoxyphenyl)prop-2-enal;
(E)-3-(4-methoxyphenyl)prop-2-enal;
1-benzofuran-2-carboxaldehyde;
2-phenyl-2-butenal; or also
5-methyl-2-phenyl-2-hexenal.

The aldehyde borne by an aromatic ring, itself optionally substituted moreover, can be chosen from
vanilline;
ethylvanilline;
vanillyl acetate;
benzaldehyde;
anisaldehyde.
cinnamaldhyde;
α-amylcinnamaldehyde (JASMONAL™);
α-hexylcinnamaldehyde;
(E)-3-(2-methoxyphenyl)prop-2-enal;
(E)-3-(4-methoxyphenyl)prop-2-enal;
α-methylcinnamaldehyde;
1-benzofuran-2-carboxaldehyde;
2-phenyl-2-butenal; or also
5-methyl-2-phenyl-2-hexenal.

Preferentially according to the invention, the aldehyde borne by an aromatic ring, itself optionally substituted moreover, can be chosen from
vanilline;
ethylvanilline;
vanillyl acetate;
benzaldehyde; or also
anisaldehyde.

Under preferential conditions for implementation of the second variant of the invention described above, the first aldehyde can be chosen preferably from the acyclic and non-terpenic aliphatic aldehydes, the non-terpenic alicyclic aldehydes, the terpenic aldehydes and the aliphatic aldehydes substituted by an aromatic group, the second aldehyde can be chosen preferably from the aldehydes which possess an unsaturation of non-aromatic type borne by the alpha carbon.

Quite particularly, the first aldehyde can be chosen from the aliphatic or acyclic and non-terpenic aliphatic aldehydes and the second from the terpenic aldehydes possessing an unsaturation on the alpha carbon referred to above.

Particularly useful pairs of aldehydes can be chosen in particular from the following pairs, without any limitation:
dodecanal and myrtenal;
dodecanal and citral;
adoxal and perillaldehyde;
triplal and citral;
maceal and citral;
adoxal and myrtenal;
decanal and citral; or also
10-undecenal and myrtenal.

According to the first variant of the invention the composition can comprise the aldehyde in a quantity comprised between 0.5% and 50% of the composition, preferentially in a quantity comprised between 1% and 20% of the composition.

According to the second variant of the invention the composition can comprise the aldehydes of classes A and B in proportions relative to each other, in proportions from 80/20 to 20/80 in particular in proportions of 50/50 and in a total quantity of aldehydes comprised between 1% and 90% of the composition, preferentially in a quantity comprised between 10% and 30% of the composition.

The deodorant compositions according to the invention, in addition to their remarkable deodorant properties, also themselves possess odiferous properties optionally capable of replacing unpleasant odours with their own odour.

According to yet another variant of the invention the deodorant compositions can moreover comprise a masking agent.

These compositions can therefore comprise at least one odoriferous agent such as those conventionally used in perfumery such as alcohols, essential oils, phenolic substances, esters.

These deodorant compositions are used under all conditions where it is sought to combat unpleasant odours, of whatever origin.

The compositions according to the invention can also contain specific substances, such as for example bactericides.

These deodorant compositions are advantageously formulated according to the usual techniques.

This is why a subject of the present Application is also deodorant products characterized in that they contain the compositions described above.

These products can be presented in the form of aerosol sprays, impregnated solid supports, liquids, cremes, powders, etc. They can be produced according to the methods known to a person skilled in the art.

A subject of the invention is also the use of a compound of the family of acetylenic ketones corresponding to formula 1 in a deodorant composition, particularly in deodorant compositions comprising at least one aldehyde chosen from the acyclic and non-terpenic aliphatic aldehydes, the non-terpenic alicyclic aldehydes, the terpenic aldehydes, the aliphatic aldehydes substituted by an aromatic group, the bifunctional aldehydes, the aldehydes possessing a non-aromatic unsaturation borne by the carbon in the alpha position of the aldehyde function, the aldehydes possessing an unsaturation in the alpha position of the aldehyde function conjugated with an aromatic ring and the aldehydes the function of which is borne by an aromatic ring, and even more preferentially in a deodorant composition comprising a mixture of at least one first aldehyde (aldehyde of class A) chosen from the acyclic and non-terpenic aliphatic aldehydes, the non-terpenic alicyclic aldehydes, the terpenic aldehydes, the aliphatic aldehydes substituted by an aromatic group and the bifunctional aldehydes and at least one second aldehyde (aldehyde of class B) chosen from the aldehydes possessing a non-aromatic unsaturation borne by the carbon in the alpha position of the aldehyde function, the aldehydes possessing an unsaturation in the alpha position of the aldehyde function conjugated with an aromatic ring and the aldehydes the function of which is borne by an aromatic ring.

Other advantages, aims and characteristics may become apparent from the description which follows, given by way of explanation and in no way limitative, of the attached drawings in which.

EXPERIMENTAL PART

Figure 1:
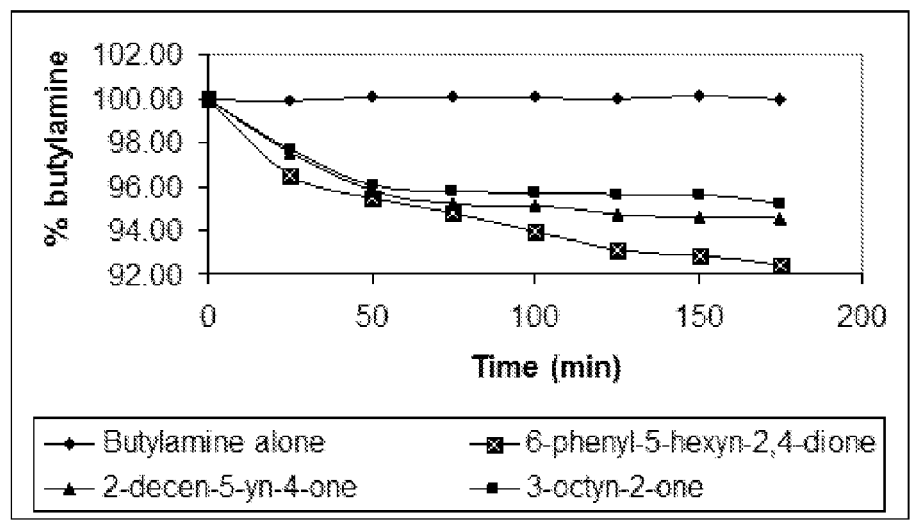
FIG. 1 illustrates the degradation of butylamine under the effect of α-acetylenic ketones according to the invention.

The examples which follow illustrate the present invention, without however limiting it.

Preparation of the α-Acetylenic Ketones

I—Disubstituted Acetylenic Ketones
R—CO—C≡C—R$_1$ 1.1 Preparation of 4-decyn-3-one (Inert Atmosphere)

A 1-liter reactor was loaded with 345 mL of diglyme (RN 111-96-6) and 17.2 g (748 mmoles) of sodium (RN 7440-23-5) cut into pieces. After heating to a temperature slightly above the melting point of sodium accompanied by thorough stirring, 71.7 g (745 mmoles) i.e. 97.5 mL of 1-heptyne (RN 628-71-7) in solution in 100 mL of diglyme is then added four times at hourly intervals. The medium thickens to form a beige suspension. Stirring is continued for another 2 hours 30 minutes at the same temperature. The mixture is cooled down to 25-30° C. and poured slowly into a stirred solution of 64.8 g (700 mmoles) i.e. 61.0 mL of propionyl chloride (RN 79-03-8) in 600 mL of ethyl ether. An exothermic reaction takes place followed by stirring for 1 hour at no particular temperature.

After washing with 4×1 liter of water, drying and concentration under reduced pressure (25 mm Hg) 98 g of a orange-yellow liquid is obtained. The latter is fractionated under reduced pressure (2 mm Hg). The fraction the temperature of which passes 70-71° C. is collected. Yield 50 g i.e. 47%.

5-decyn-4-one, 3-octyn-2-one, 4-phenyl-3-butyn-2-one, 9-hexadecyn-8-one, 1-(2-furyl)-3-phenyl-2-propyne-1-one and 1-cyclopentyl-4-nonyn-3-one (non-limitative examples) are prepared analogously.

I.II Preparation of the Mixture of 4-nonyn-3-one and 5-nonyn-4-one

A 500-mL reactor is loaded with 13.8 g (111 mmoles) of 4-nonyne (RN 20184-91-2), 175 mL of tert-butanol (RN 75-65-0), 770 mg (4.5 mmoles) of cupric chloride dihydrate (RN 10125-13-0), and 33.4 mL (244 mmoles) of 70% tert-butyl hydroperoxide (RN 75-91-2). Accompanied by thorough stirring and under an atmosphere of pure oxygen originating from a graduated tank, the medium is heated to 60-65° C. At the end of three hours it is noted that the medium absorbs no more oxygen and has consumed the theoretical quantity.

The medium is poured over ice and extracted three times with ether. The combined organic phases are washed four times with 5% saltwater. After drying and concentration approximately 40 g of a green liquid is obtained, which is fractionated by distillation under reduced pressure (20 mm Hg). The two isomers, which are not separated, distill together between 92 and 97° C.

2-methyl-5-decyn-4-one and 9-methyl-5-decyn-4-one as well as 1-phenyl-1-pentyn-3-one (the latter in a single isomer, a single site of the starting 1-phenyl-1-pentyne being able to be oxidized) are prepared analogously.

II—True acetylenic ketones R—CO—C≡CH,
Disubstituted acetylenic ketones R—CO—C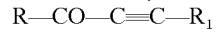C—R1

IIA—Preparation of 1-octyn-3-one

IIA-1) Preparation of 1-octyn-3-ol (Inert Atmosphere)

A 750-mL reactor is loaded with 40.1 g (400 mmoles) i.e. 49.2 mL of hexanal (RN 66-25-1) and 400 mL of anhydrous tetrahydrofuran and 100 g of a suspension of 18% sodium acetylide (RN 1066-26-8) in xylene (375 mmoles) is added by portions accompanied by stirring. An exothermic reaction takes place. Stirring is then continued for another 2 hours at no particular temperature. After hydrolysis, extractions and concentration, fractionation is carried out under reduced pressure.

It is however to be noted that a better result is obtained by using ethynylmagnesium bromide (RN 4301-14-8). This is for example the case with 1-decyn-3-ol.

IIA-2) Preparation of 1-octyn-3-one

A 1500-mL reactor is loaded with 25.24 g (200 mmoles) i.e. 29.1 mL of 1-octyn-3-ol, 600 mL of acetone and 90 mL of water. Accompanied by vigorous stirring a solution of 29.4 g (100 mmoles) of potassium dichromate of (RN 7778-50-9) in 300 mL of water and 22 mL of sulphuric acid is added over 1 hour 30 minutes. The coloration changes from orange to green. At the end, stirring is continued for another 30 minutes then 1000 mL of water is added also over 30 minutes.

After extractions with ethyl ether, washings, drying and concentration under slightly reduced pressure, 25 g of an orange liquid is obtained, which is fractionated under reduced pressure (20 mm Hg). The fraction the temperature of which passes 74-76° C. is collected.

1-phenyl-2-propyn-1-one and 1-decyn-3-one and 1-(p-methoxyphenyl)-2-propyn-1-one are prepared analogously.

IIA-3 Other Preparations 1-cyclohexyl-4-ethyl-1-hexyn-3-one, 7-tetradecyn-8-one, 2-nonyn-4-one, 9-hexadecyn-8-one and 1-(p-tolyl)-2-butyn-1-one are prepared analogously, using the salt of a substituted alkyne (Na—C≡C—R).

III—Evaluation of the Effect of the Compositions According to the Invention on Unpleasant Odours Organoleptic tests, with formulae containing or not containing acetylenic ketones described previously record significant reduction of complex unpleasant odours (cooking, toilet, tobacco odours).

III-1 Protocol

The olfactory test is carried out with a panel of 25 experts. The α-acetylenic ketones to be tested are prepared at a concentration of 1 mol/L in dipropylene glycol.

The reference malodorous solution is also prepared at a concentration of 1 mol/L.

A first pillbox contains 1 g of the reference malodorous solution.

An equimolar mixture of 1 g of a solution of α-acetylenic ketone and 1 g of solution of reference malodorous solution is placed in other pillboxes (1 pillbox per α-acetylenic ketone to be tested).

The unpleasant odour released by the first pillbox is assigned the reference 10 (reference malodorous solution).

Using a Latin square (table indicating the order to be followed by each judge in the testing panel in order to avoid bias), the other pillboxes are evaluated in comparison with the first.

The results are then converted to percentages of residual unpleasant odour.

The following α-acetylenic ketones are tested on different solutions of reference malodorous solution:
A: 6-phenyl-5-hexyn-2,4-dione of formula $C_6H_5$—C≡C—CO—$CH_2$—CO—$CH_3$;
B: 4-phenyl-3-butyn-2-one of formula $C_6H_5$—C≡C—CO—$CH_3$;
C: 2-decen-5-yn-4-one of formula $C_4H_9$—C≡C—CO—CH═CH—$CH_3$;
D: 7-tetradecyn-6-one of formula $C_6H_{13}$—C≡C—CO—$O_5H_{11}$ III-2 Test of Effectiveness on butylamine

| | % of residual unpleasant odour |
|---|---|
| 1 g of butylamine (Reference) | 100 |
| 1 g of butylamine + 1 g of A | 30 |
| 1 g of butylamine + 1 g of B | 28 |
| 1 g of butylamine + 1 g of C | 25 |
| 1 g of butylamine + 1 g of D | 58 |

A clear reduction in the residual odour is noted

III-3 Test of Effectiveness on thioglycolic Acid

| | % of residual unpleasant odour |
|---|---|
| 1 g of acid thioglycolic (Reference) | 100 |
| 1 g of acid thioglycolic + 1 g of A | 57 |
| 1 g of acid thioglycolic + 1 g of B | 30 |
| 1 g of acid thioglycolic + 1 g of C | 57 |
| 1 g of acid thioglycolic + 1 g of D | 49 |

A clear reduction in the residual odour is noted

III—Test of Effectiveness on an Unpleasant Cooking Odour

This test aims to show the potentiating effect of the α-acetylenic ketones on an already known deodorant, Neutral 1.

An unpleasant cooking odour is prepared by mixing the following different compounds:

| Compound | % in the mixture | Characteristic odour |
|---|---|---|
| Trimethylamine | 0.10 | Fish |
| Dimethyl sulphide | 0.13 | Cabbage |
| Dimethyl disulphide | 0.02 | Onion |
| Pyridine, 2-methanethiol 10% | 0.50 | Rotten meat |
| Isovaleric acid | 0.70 | Sweat, Cheese |
| Butyric acid | 0.30 | Cheese |
| Capric acid | 0.50 | Fermented Cheese |
| Methyl amyl ketone | 0.10 | Strong blue cheese |
| 2-Mercaptopropanone | 0.06 | Meat, Sulphuousr, Mould |
| Diallyl disulphide | 0.05 | Garlic |
| Butyl butyryllactate | 1.30 | Sour milk |
| Methional | 0.02 | Old potato |
| Indole 1% | 0.14 | Rotten vegetable, mould |
| Diacetyl | 0.10 | Rancid butter |
| Hexanoic acid | 0.20 | Old cheese |
| Guaiacol | 0.04 | Cooked meat |
| Propylene glycol | 95.74 | Support |

20 µL of this unpleasant odour is deposited on a 1 $cm^2$ cellulose support, which is placed in a 3 $m^3$ odour chamber. This enclosure serves as a reference.

In the same way, identical closed enclosures containing the unpleasant odour to which 10 µL of Neutral 1 alone, i.e. 10 µL of a mixture of Neutral and of an α-acetylenic ketone (in a proportion of 99/1) are also prepared.

The testing panel then evaluates the odour in each of the enclosures, according to the order defined by a Latin square and in comparison with the reference enclosure containing the unpleasant odour alone.

The following α-acetylenic ketones are tested on the reference malodorous solution:

E: Neutral 1
F: Neutral 1 and 2,2-dimethyl-4-hexyn-3-one of formula $CH_3—C≡C—CO—C(CH_3)_3$
G: Neutral 1 and 5-decyn-4-one of formula $C_4H_9—C≡C—CO—C_3H_7$
H: Neutral 1 and 2,5-heptadiyn-4-one of formula $H_3C—C≡C—CO—C≡C—CH_3$
I: Neutral 1 and 3-octyn-2-one of formula $C_4H_9—C≡C—CO—CH_3$ Formula of Neutral 1:

| Compound | Quantity (vol./vol.) |
|---|---|
| Phenylacetaldehyde (A) | 0.32% |
| Hydroxycitronellal (A) | 1.63% |
| α-Hexylcinnamaldehyde (B) | 19.09% |
| Lilial (A) | 7.91% |
| DiPropyleneGlycol | qsf 100 |

| | % of residual unpleasant odour |
|---|---|
| Cooking odour alone (OdC = Reference) | 100 |
| OdC + E | 39 |
| OdC + F | 32 |
| OdC + G | 24 |
| OdC + H | 30 |
| OdC + I | 36 |

The addition of a small of α-acetylenic ketone in addition to the Neutral improves the effectiveness of Neutral 1 against the unpleasant cooking odour.

III-5 Test of Effectiveness on an Unpleasant Tobacco Odour

An unpleasant tobacco odour is prepared from ash and cigarette ends. 20 g of this odour is deposited in a 3 m³ odour chamber.

Cloth towels are deposited in the enclosure and left for 24 hours in order to become impregnated with the tobacco odour. 100 μL of Neutral 2 is then sprayed on the linen cloth.

Similarly towels brought into contact with the tobacco odour are prepared and mixtures of anti-tobacco Neutral 2 and a small α-acetylenic ketone (in a proportion of 99/1) or a mixture of two small α-acetylenic ketones (in a proportion of 99/0.5/0.5) are sprayed on the towels.

The panel then evaluates the quantity of unpleasant tobacco odour on the towels in comparison with towels which had received no treatment against the unpleasant odour.

The following α-acetylenic ketones are tested on the reference malodorous solution:

J: Neutral 2,
K: Neutral 2 and 2,5-heptadiyn-4-one of formula $H_3C—C≡C—CO—C≡C—CH_3$,
L: Neutral 2 and 1-octyn-3-one of formula $C_5H_{11}—CO—C≡CH$,
M: Neutral 2 and 5-decyn-4-one of formula $C_4H_9—C≡C—CO—C_3H_7$,
N: Neutral 2 and 1-phenyl-2-propyn-1-one of formula $C_6H_5—CO—C≡CH$, and 6-phenyl-5-hexyn-2,4-dione of formula $C_6H_5—C≡C—CO—CH_2—CO—CH_3$,
O: Neutral 2 and 4-phenyl-3-butyne-2-one of formula $C_6H_5—C≡C—CO—CH_3$, and 1-phenyl-2-propyn-1-one of formula $C_6H_5—CO—C≡CH$, Formula of Neutral 2:

| Compound | Quantity (vol./vol.) |
|---|---|
| Lilial (A) | 10% |
| Anisaldehyde | 20% |
| α-Hexylcinnamaldehyde (B) | 69% |
| Butylhydroxytoluene | qsf 100 |

Spray formula:

| Compound | Quantity (v/v) |
|---|---|
| Ethyl alcohol | 15.0 |
| Sodium lauroyl sarcosinate | 0.5 |
| Sodium carbonate | 2.0 |
| Sodium dioctyl sulphosuccinate | 0.5 |
| Neutral 2 | 0.5 |
| Demineralized water | qsf 100 |

| | % of residual unpleasant odour |
|---|---|
| Tobacco odour alone (OdT = Reference) | 100 |
| OdT + J | 65 |
| OdT + K | 33 |
| OdT + L | 39 |
| OdT + M | 51 |
| OdT + N | 51 |
| OdT + O | 55 |

The effectiveness of Neutral 2 is improved by the addition of at least one α-acetylenic ketone.

III-6 Test of Effectiveness on an Unpleasant Toilet Odour

An unpleasant toilet odour is prepared by mixing the following different compounds:

| Compound | % in the mixture | Characteristic odour |
|---|---|---|
| Scatole | 0.90 | Faecal |
| Thionaphthol | 0.90 | Faecal, sulphurous |
| Thioglycolic acid | 21.18 | Sulphurous |
| Hexanoic acid | 6.00 | Sweat |
| p-Cresyl isovalerate | 2.18 | Faecal, sweat |
| N-Methyl morpholine | 6.00 | Urine |
| Dipropylene Glycol (DPG) | qsf 100 | |

20 μL of this unpleasant odour is deposited in the water of a toilet bowl in a cubicle. 20 μL of unpleasant odour as well as 20 μL of a Neutral 3 which is active against the unpleasant toilet odour are deposited in another cubicle.

In other cubicles, an α-acetylenic ketone in a proportion of 99/1 with Neutral 3 is added in addition.

The quantity of unpleasant toilet odour in each cubicle is then evaluated by the testing panel.

The following α-acetylenic ketones are tested on the reference malodorous solution:
P: Neutral 3;
Q: Neutral 3 and 2,5-heptadiyn-4-one of formula $H_3C—C≡C—CO—C≡C—CH_3$;
R: Neutral 3 and 2,2-dimethyl-4-hexyn-3-one of formula $CH_3—C≡C—CO—C(CH_3)_3$;
S: Neutral 3 and 1-octyn-3-one of formula $C_5H_{11}—CO—C≡CH$;
T: Neutral 3 and 5-decyn-4-one of formula $C_4H_9—C≡C—CO—C_3H_7$;

Formula of Neutral 3:

| Compound | Quantity (vol./vol.) |
| --- | --- |
| Citral | 3.5% |
| Orange terpenes | 1.5% |
| Linalyl Acetate | 11.0% |
| Linalol | 23.0% |
| Citral DEA | 0.3% |
| Eugenol | 5.0% |
| 3Z-hexenyl acetate 10% DPG | 5.0% |
| α-hexyl cinnamic aldehyde | 15.0% |
| Hederile 10% DPG | 1.0% |
| Butylhydroxytoluene 10% DPG | 0.2% |
| Dipropylene Glycol (DPG) | qsf 100% |

| | % of residual unpleasant odour |
| --- | --- |
| Toilet odour alone (OdT = Reference) | 100 |
| OdT + P | 47 |
| OdT + Q | 19 |
| OdT + R | 20 |
| OdT + S | 21 |
| OdT + T | 23 |

The effectiveness of Neutral 3 is improved by the addition of at least one α-acetylenic ketone.

IV—Chemical Reactivity

Parallel tests contribute to recording the reactivity of the keto-alkynes. They are carried out by a mole to mole reaction of a keto-alkyne with a substance responsible for an unpleasant odour. The reaction is carried out at ambient temperature in THF.

40 acetylenic ketones are tested in order to verify their reactivity (their potential to reduce unpleasant odours).

IV-1 Reactivity with piperidine

A substrate, piperidine, is used to verify this reactivity. The reactivity is measured by the signal obtained in gaseous phase chromatography (respective signal obtained after a reaction time t=5 min, t=2 hours and t=5 hours measured for the keto-alkyne, for the reaction product).

IV-1.1 Reaction Time 5 Minutes

| Compounds | t = 5 min |
| --- | --- |
| $C_6H_5—CO—C≡CH$ | 0 |
| $CH_3—C≡C—CO—C≡C—CH_3$ | 0 |
| $CH_3O—C_6H_4—CO—C≡CH$ | 0 |
| $C_6H_5—C≡C—CO—C_4H_3O$ (furyl) | 0 |
| $C_3H_7—C≡C—CO—C≡C—C_3H_7$ | 0 |
| $C_6H_5—CO—C≡C—CO—C_6H_5$ | 1 |
| $C_7H_{15}—CO—C≡CH$ | 4 |
| $C_5H_{11}—C≡C—CO—C_4H_3O$ (furyl) | 5 |
| $C_5H_{11}—CO—C≡CH$ | 8 |
| $CH_3—C≡C—CO—C_6H_4—(p-CH_3)$ | 9 |

Five acetylenic ketones show a very strong reactivity vis-à-vis the substrate used. 5 min after the two reagents are brought into contact, the keto-alkyne has totally disappeared and the formation of the reaction substance reaches its maximum.

Five other acetylenic ketones show a strong reactivity with a 90 to 99% disappearance of the reagents after 5 minutes.

IV-1.2 Reaction Time 2 Hours

Examination of the reactivity after reaction for 2 hours shows the disappearance of more than 90% of the acetylenic ketones (and the appearance of the reaction product) with more than half of the products tested (24 out of 40).

| Compounds | t = 2 hours |
| --- | --- |
| $C_6H_5—CO—C≡CH$ | 0 |
| $CH_3—C≡C—CO—C≡C—CH_3$ | 0 |
| $CH_3O—C_6H_4—CO—C≡CH$ | 0 |
| $C_5H_{11}—C≡C—CO—C_4H_3O$ (furyl) | 0 |
| $CH_3—C≡C—CO—C_6H_3(OCH_3)_2$ | 0 |
| $C_6H_5—CO—C≡C—CO—C_6H_5$ | 0 |
| $C_3H_5—C≡C—CO—C_6H_4—CH_3$ | 0 |
| $C_6H_5—C≡C—CO—C_4H_3O$ (furyl) | 0 |
| $CH_3—C≡C—CO—C_6H_4—(p-CH_3)$ | 0 |
| $C_3H_7—C≡C—CO—C≡C—C_3H_7$ | 0 |
| $C_2H_5—CO—C≡C—(CH_2)_4—C≡C—CO—C_2H_5$ | 1 |
| $C_6H_5—C≡C—CO—C_2H_5$ | 1 |
| $C_6H_5—C≡C—CO—CH_2—CO—CH_3$ | 2 |
| $C_6H_5—C≡C—CO—CH_3$ | 2 |
| $CH_3—C≡C—CO—C(CH_3)_3$ | 2 |
| $CH_3—C≡C—CO—C_5H_{11}$ | 4 |
| $C_7H_{15}—CO—C≡CH$ | 4 |
| $C_3H_7—CH_2—C≡C—CO—CH(CH_3)_2$ | 5 |
| $C_3H_7—CO—C≡C—CH_2—CH(CH_3)_2$ | |
| $C_5H_{11}—CO—C≡CH$ | 7 |
| $C_6H_5—C≡C—CO—C_4H_9$ | 7 |
| $C_3H_5—C≡C—CO—CH(C_2H_5)—C_4H_9$ | 8 |
| $(CH_3)_2CH—C_2H_4—C≡C—CO—CH_2—CH(CH_3)_2$ | 8 |
| $C_5H_{11}—C≡C—CO—C_2H_5$ | 9 |
| $C_6H_{13}—C≡C—CO—C_7H_{15}$ | 9 |

IV-1.3 Reaction Time 5 Hours

Examination of the reactivity after reaction for 5 hours shows the disappearance of more than 90% of the acetylenic ketones (and the appearance of the reaction product) with virtually all of the products tested (36 out of 40).

Three acetylenic ketones react strongly with a disappearance of 55 to 83%. Only one substance shows no reactivity.

| Compounds | t = 5 hours |
|---|---|
| $CH_3-C\equiv C-CO-C(CH_3)_3$ | 0 |
| $CH_3-C\equiv C-CO-C\equiv C-CH_3$ | 0 |
| $CH_3O-C_6H_4-CO-C\equiv CH$ | 0 |
| $C_5H_{11}-C\equiv C-CO-C_4H_3O$ (furyl) | 0 |
| $CH_3-C\equiv C-CO-C_6H_3(OCH_3)_2$ | 0 |
| $C_6H_5-CO-C\equiv C-CO-C_6H_5$ | 0 |
| $C_3H_5-C\equiv C-CO-C_6H_4-(p\text{-}CH_3)$ | 0 |
| $C_6H_5-C\equiv C-CO-C_4H_3O$ (furyl) | 0 |
| $CH_3-C\equiv C-CO-C_6H_4-(p\text{-}CH_3)$ | 0 |
| $C_3H_7-C\equiv C-CO-C\equiv C-C_3H_7$ | 0 |
| $C_2H_5-CO-C\equiv C-(CH_2)_4-C\equiv C-CO-C_2H_5$ | 0 |
| $C_6H_5-CO-C\equiv CH$ | 0 |
| $C_6H_5-C\equiv C-CO-CH_3$ | 0 |
| $C_5H_{11}-C\equiv C-CO-C_2H_5$ | 1 |
| $C_3H_5-C\equiv C-CO-CH(C_2H_5)-C_4H_9$ | 1 |
| $C_6H_{13}-C\equiv C-CO-C_7H_{15}$ | 1 |
| $CH_3-C\equiv C-CO-C_5H_{11}$ | 1 |
| $C_6H_5-C\equiv C-CO-CH_2-CO-CH_3$ | 1 |
| $C_6H_5-C\equiv C-CO-C_2H_5$ | 1 |
| $C_6H_{13}-C\equiv C-CO-C_5H_{11}$ | 2 |
| $C_4H_9-C\equiv C-CO-CH_3$ | 2 |
| $C_2H_5-CO-C\equiv C_6(CH_2)_4-C\equiv CH$ | 2 |
| $C_4H_9-C\equiv C-CO-(CH_2)_2-C_5H_9$ | 3 |
| $C_3H_7-C\equiv C-CO-C_4H_9$ | 3 |
| $C_3H_7-CH_2-C\equiv C-CO-CH(CH_3)_2$ | 4 |
| $C_3H_7-CO-C\equiv C-CH_2-CH(CH_3)_2$ | |
| $C_7H_{15}-CO-C\equiv CH$ | 4 |
| $C_3H_7-C\equiv C-CO-CH(CH_3)_2$ | 6 |
| $C_4H_9-C\equiv C-CO-C_3H_7$ | 6 |
| $C_4H_9-C\equiv C-CO-C_3H_5$ (cyclopropyl) | 7 |
| $(CH_3)_2CH-C_2H_4-C\equiv C-CO-CH_2-CH(CH_3)_2$ | 7 |
| $C_6H_5-C\equiv C-CO-C_4H_9$ | 7 |
| $C_5H_{11}-CO-C\equiv CH$ | 8 |
| $C_4H_9-C\equiv C-CO-C_6H_{11}$ | 8 |
| $(CH_3)_2CH-C_2H4-C\equiv C-CO-C(CH_3)_3$ | 9 |
| $C_3H_7-CH_2-C\equiv C-CO-C_2H_5$ | 10 |
| $C_3H_7-CO-C\equiv C-CH_2-C_2H_5$ | |
| $C_4H_9-C\equiv C-CO-CH=CH-CH_3$ | 17 |
| $(CH_3)_2CH-C_2H_4-C\equiv C-CO-CH(C_2H_5)-C_4H_9$ | 23 |
| $C_6H_{11}-C\equiv C-CO-CH(C_2H_5)_2$ | 45 |
| $(CH_3)_2CH-CO-C\equiv C-CH_2-O-CH_2-C\equiv C-CO-CH(CH_3)_2$ | 87 |

IV-2 Reactivity with the Mercaptans

Three sulphurous compounds serve as support for the reactivity of the acetylenic ketones (butanethiol, 2-phenylethanethiol and α-toluenethiol).

Five acetylenic ketones which reacted strongly with piperidine were tested.

The operating conditions are identical to those previously described for piperidine (Mole to mole reaction of a ketoalkyne with a mercaptan).

The reaction is carried out at ambient temperature in THF.

The reactivity is monitored by chromatographic measurements which are carried out for 3 hours after the following reaction times:

t=5 min, t=40 min, t=75 min, t=110 min, t=145 min, t=180 min.

IV-2.1. Reactivity with 2-phenylethanethiol

| | Concentration of the acetylenic ketones (% GC) Time (minutes) | | | | | |
|---|---|---|---|---|---|---|
| | 5 | 40 | 75 | 110 | 145 | 180 |
| $C_6H_5-CO-C\equiv CH$ | 3 | — | — | — | — | — |
| $CH_3O-C_6H_4-CO-C\equiv CH$ | 6 | — | — | — | — | — |
| $CH_3-C\equiv C-CO-C\equiv C-CH_3$ | 90 | 20 | 2 | — | — | — |
| $C_6H_5-C\equiv C-CO-C_4H_3O$ (furyl) | 88 | 35 | 24 | 13 | — | — |
| $C_3H_7-C\equiv C-CO-C\equiv C-C_3H_7$ | 87 | 46 | 40 | 35 | 29 | 26 |

Two of these substances react instantaneously, two others disappear after 2 hours of reaction, the fifth reacts strongly after only 3 hours of reaction.

Three other acetylenic ketones, 1-cyclopentyl-4-nony-3-one, ($C_4H_9-C\equiv C-CO-C_2H_4-C_5H_9$), 1-cyclopropyl-2-heptyn-1-one ($C_4H_9-C\equiv C-CO-C_3H_5$) and 5-decyn-4one ($C_4H_9-C\equiv C-CO-C_3H_7$) do not react with 2-phenylethanethiol. The addition of a catalyst promotes their reactivity very slightly. -

IV-2.2. Reactivity with Butanethiol

|  | Concentration of the acetylenic ketones (% GC) Time (minutes) | | | | | |
| --- | --- | --- | --- | --- | --- | --- |
|  | 5 | 40 | 75 | 110 | 145 | 180 |
| $C_6H_5-CO-C\equiv CH$ | 2 | — | — | — | — | — |
| $CH_3O-C_6H_4-CO-C\equiv CH$ | 12 | tr | — | — | — | — |
| $CH_3-C\equiv C-CO-C\equiv C-CH_3$ | 78 | 14 | 6 | 2 | — | — |
| $C_6H_5-C\equiv C-CO-C_4H_3O$ (furyl) | 95 | 82 | 67 | 53 | 45 | 39 |
| $C_3H_7-C\equiv C-CO-C\equiv C-C_3H_7$ | 96 | 86 | 75 | 60 | 44 | 40 |

The reactivity with butanethiol is fairly similar to that of 2-phenylethanethiol.

IV-2.3. Reactivity with Toluenethiol

|  | Concentration of the acetylenic ketones (% GC) Time (minutes) | | | | | |
| --- | --- | --- | --- | --- | --- | --- |
|  | 5 | 40 | 75 | 110 | 145 | 180 |
| $CH_3-C\equiv C-CO-C\equiv C-CH_3$ | 2 | — | — | — | — | — |
| $C_6H_5-C\equiv C-CO-C_4H_3O$ (furyl) | 16 | — | — | — | — | — |

The reaction with toluenethiol is very rapid with two targets and slower with the three other targets tested.

V—Chromatographic Tests

Gas chromatography: use of an internal standard, ethyl decanoate.

The peaks corresponding to each α-acetylenic ketone, to butylamine, to the internal standard and to the solvent are determined.

The surface areas of the peaks make it possible to determine the residual quantity of butylamine (unpleasant odour).

Chromatographic analyses are carried out every 25 minutes in order to establish kinetics.

The results are presented in FIG. 1.

Used alone in a proportion of 1/10 (α-acetylenic ketone/butylamine), the α-acetylenic ketones lead to a 4 to 8% reduction in the quantity of butylamine in less than 3 hours.

The effect of Neutral 2 alone on butylamine and the effect of Neutral 2 to which 1% α-acetylenic ketone is added are tested in comparison with the previous tests.

Figure 2:
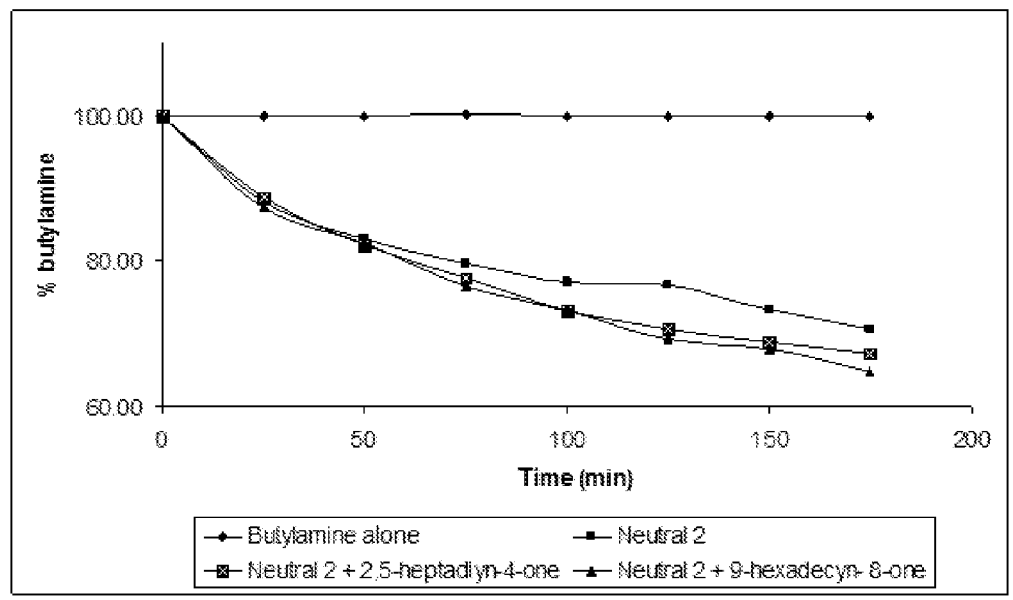
FIG. 2 illustrates the degradation of butylamine under the effect of a known neutralizing agent to which an α-acetylenic ketone according to the invention is added.

The results are presented in FIG. 2.

As increase in the effectiveness of Neutral 2 on the quantity of butylamine is noted.

The tests described in paragraphs IV and V demonstrate that the α-acetylenic ketones exert their deodorant effect by physically destroying the malodorous molecules. This effect is therefore not a simple masking effect.

VI—Deodorant Compositions

VI-1. Aerosol Air Freshener

An aqueous air spray perfumed with a "magnolia" neutralizer containing the following aldehydes:

| Phenylacetaldehyde (A) | 0.32% |
| --- | --- |
| Hydroxycitronellal (A) | 1.63% |
| α-Hexylcinnamaldehyde (B) | 19.09% |
| Lilial (A) | 7.91% |
| 2,4-Dimethyl-3-cyclohexen-1-carboxaldehyde (A) | 0.15% |
| DPG | Qsf 100 |

VI-2. Deodorant and Disinfectant Liquid for Floors

The aldehydes can also be formulated in the form of acetals in order to reduce the intrinsic odour of the neutralizer and increase the duration of action. It is known that an acetal is hydrolyzed in acid medium releasing the corresponding aldehyde.

By way of examples, here are a few acetals with a faint odour which can be used in a surface deodorant: propionaldehyde DEA, phenylacetaldehyde-methanol acetal, citral diethylacetal, hydroxycitronnellal dimethylacetal, benzaldehyde diethylacetal.

Surface Deodorant Formula:

| Compound | Quantity (v/v) |
| --- | --- |
| Ethyl alcohol | 15.0 |
| Sodium lauroyl sarcosinate | 0.5 |
| Sodium carbonate | 2.0 |
| Sodium dioctyl sulphosuccinate | 0.5 |
| Neutral 2 | 0.5 |
| Demineralized water | qsf 100 |

The invention claimed is:

1. A method for destroying malodorous molecules using a deodorant composition, wherein said deodorant composition comprises at least one compound of the family of the a-acetylenic ketones corresponding to general formula 1

$$R-(CO)k-C\equiv C-(A)-(C\equiv C)m-(CO)n-R1 \quad (1)$$

in which

R and R1 can represent, independently or simultaneously, a radical selected from the group consisting of
- an alkyl chain comprising from 1 to 9, linear or branched, substituted or unsubstituted,
- a cycloalkane comprising from 3 to 8, substituted or unsubstituted;
- a furan ring, saturated or unsaturated, substituted or unsubstituted;
- a pyran ring, saturated or unsaturated, substituted or unsubstituted;
- an aromatic ring comprising from 6 to 8 carbon atoms, substituted or unsubstituted; and
- a hydrogen atom, A represents a group selected from the group consisting of —$(CH_2)x$ with x representing an integer with a value from 0 to 6, (CO)l with l representing an integer with a value of 0 or 1, or also a —$(CH_2)y$-O—$(CH_2)z$-chain formation with y and z representing, simultaneously or independently, an integer with a value from 0 to 6, wherein x+y does not exceed the value of 6;

k, m and n are, simultaneously or independently, an integer with a value of 0 or 1, wherein k and n do not simultaneously have a value of 0 if l is equal to 0;

with the exception of 2-methyl-4-nonyn-3-one of formula $C_4H_9-C\equiv C-CO-CH(CH_3)_2$ in the deodorant composition.

2. The method of claim 1, wherein the compound of formula 1 is selected from the group consisting of
1-octyn-3-one of formula $C_5H_{11}-CO-C\equiv CH$;
3-octyn-2-one of formula $C_4H_9-C\equiv C-CO-CH_3$;

4-octyn 3-one of formula $C_3H_7-C\equiv C-CO-C_2H_5$;
4-nonyn-3-one of formula $C_3H_7-CH_2-C\equiv C-CO-C_2H_5$;
2-nonyn-4-one of formula $CH_3-C\equiv C-CO-O_5H_{ii}$;
5-nonyn-4-one of formula $C_3H_7-CO-C\equiv C-CH_2-C_2H_5$;
1-decyn-3-one of formula $C_7H_{15}-CO-C\equiv CH$;
4-decyn-3-one of formula $C_5H_{11}-C\equiv C-CO-C_2H_5$;
6-decyn-5-one of formula $C_3H_7-C\equiv C-CO-C_4H_9$;
5-decyn-4-one of formula $C_4H_9-C\equiv C-CO-C_3H_7$;
2-decen-5-yn-4-one of formula $C_4H_9-C\equiv C-CO-CH=CH-CH_3$;
1-(p-methoxyphenyl)-2-propyn-1-one of formula $H_3C-O-C_6H_4-CO-C\equiv CH$;
1-cyclopropyl-2-heptyn-1-one of formula $C_4H_9-C\equiv C-CO-C_3H_5$ cyclopropyl);
2-methyl-5-decyn-4-one of formula $C_4H_9-C\equiv C-CO-CH_2-CH(CH_3)_2$;
9-methyl-5-decyn-4-one of formula $C_3H_7-CO-C\equiv C-CH_2-CH_2-CH(CH_3)_2$;
2-methyl-4-octyn-3-one of formula $C_3H_7-C\equiv C-CO-CH(CH_3)_2$;
1-phenyl-2-propyn-1-one of formula $C_6H_5-CO-C\equiv CH$;
4-phenyl-3-butyn-2-one of formula $C_6H_5-C\equiv C-CO-CH_3$;
5-phenyl-4-pentyn-3-one of formula $C_6H_5-C\equiv C-CO-C_2H_5$;
6-phenyl-5-hexyn-2,4-dione of formula $C_6H_5-C\equiv C-CO-CH_2-CO-CH_3$;
1-phenyl-1-heptyn-3-one of formula $C_6H_5-C\equiv C-CO-C_4H_9$;
1-(2-furyl)-3-phenyl-2-propyn-1-one of formula $C_6H_5-C\equiv C-CO-C_4H_3O$ furyl);
1-(2-furyl)-2-octyn-1-one of formula $C_5H_{11}-C\equiv C-CO-C_4H_3O$ (furyl);
$C_6H_5-C\equiv C-CO-C_4H_3O$ (furyl);
3-cyclopropyl-1-(p-tolyl)-2-propyn-1-one of formula $C_3H_2-C\equiv C-CO-C_6H_4-CH_3$;
1-cyclopropyl-4-methyl-1-hexyn-3-one of formula $C_3H_5-C\equiv C-CO-CH(C_2H_5)-CH_3$ (cyclopropyl);
9-hexadecyn-8-one of formula $C_6H_{13}-C\equiv C-CO-C_7H_{15}$;
5-ethyl-11-methyl-7-dodecyn-6-one of formula $(CH_3)_2CH-C_2H_4-C\equiv C-CO-CH(C_2H_5)-C_4H_9$;
7-tetradecyn-6-one of formula $C_6H_{13}-C\equiv C-CO-O_5H_{11}$;
1-cyclohexyl-4-ethyl-1-hexyn-3-one of formula $C_6H_{11}-C\equiv C-CO-CH(C_2H_5)_2$ (cyclohexyl);
1-cyclopentyl-4-nonyn-3-one of formula $C_4H_9-C\equiv C-CO-C_2H_4-O_5H_9$ (cyclopentyl);
1-cyclohexyl-2-heptyn-1-one of formula $C_4H_9-C\equiv C-CO-C_6H_{11}$ (cyclohexyl);
1-(p-tolyl)-2-butyn-1-one of formula $CH_3-C\equiv C-CO-C_6H_4-(p-CH_3)$;
2,2,8-trimethyl-4-nonyn-3-one of formula $(CH_3)_2CH-C_2H_4-C\equiv C-CO-C(CH_3)_3$;
2,2-dimethyl-4-hexyn-3-one of formula $CH_3-C\equiv C-CO-C(CH_3)_3$;
1,4-diphenyl-2-butyn-1,4-dione of formula $C_6H_5-CO-C\equiv C-CO-C_6H_5$;
5-decyn-2,4-dione of formula $C_4H_9-C\equiv C-CO-CH_2-CO-CH_3$;
1-(3,4-dimethoxyphenyl)-2-butyn-1-one of formula $CH_3-C\equiv C-CO-C_6H_3-(OCH_3)_2$;
2,5-heptadiyn-4-one of formula $H_3C-C\equiv C-CO-C\equiv C-CH_3$;
3-hexyn-2,5-dione of formula $CH_3-CO-C\equiv C-CO-CH_3$;
4-octyn-3,6-dione of formula $C_2H_5-CO-C\equiv C-CO-C_2H_5$;
2,7-dimethyl-4-octyn-3,6-dione of formula $(CH_3)_2CH-CO-C\equiv C-CO-CH(CH_3)_2$;
2,7-dimethyl-4-octyn-3-one of formula $(CH_3)_2CH-CH_2-C\equiv C-CO-CH(CH_3)_2$;
4,7-undecadiyn-6-one of formula $C_3H_7-C\equiv C-CO-C\equiv C-C_3H_7$;
5-decyn-4,7-dione of formula $C_3H_7-CO-C\equiv C-CO-C_3H_7$;
2,9-dimethyl-5-decyn-4,7-dione of formula $(CH_3)_2CH-CH_2-CO-C\equiv C-CO-CH_2-CH(CH_3)_2$;
6-dodecyn-5,8-dione of formula $C_4H_9-CO-C\equiv C-CO-C_4H_9$;
2,11-dimethyl-6-dodecyn-5,8-dione of formula $(CH_3)_2CH-C_2H_4-CO-C\equiv C-CO-(CH_2)_2-CH(CH_3)$;
2,9-dimethyl-5-decyn-4-one of formula $(CH_3)_2CH-C_2H_4-C\equiv C-CO-CH_2-CH(CH_3)_2$;
7-tetradecyn-6,9-dione of formula $C_5H_{11}-CO-C\equiv C-CO-O_5H_{11}$;
4,10-undecadiyn-3-one of formula $HC\equiv C-C_4H_8-C\equiv C-CO-C_2H_5$;
2,12-dimethyl-7-oxa-4,9-tridecadiyn-3,11-dione of formula $(CH_3)_2-CO-C\equiv C-CH_2-O-CH_2-C\equiv C-CO-CH(CH_3)_2$; and
4,10-tetradecadiyn-3,12-dione of formula $C_2H_5-CO-C\equiv C-C_4H_8-C\equiv C-CO-C_2H_5$.

3. The method of claim 1, wherein the compound of formula 1 is a pair of compounds of formula 1 selected from the group consisting of the pairs 1-phenyl-2-propyn-1-one/1-decyn-3-one;
1-(2-furyl)-2-octyn-1-one/1-decyn-3-one;
1-(2-furyl)-3-phenyl-2-propyn-1-one/1-decyn-3-one;
1-octyn-3-one/1-decyn-3-one;
1-(p-tolyl)-2-butyn-1-one/1-decyn-3-one;
2,5-heptadiyn-4-one/1-decyn-3-one;
1-(p-methoxyphenyl)-2-propyn-1-one/1-decyn-3-one;
1,4-diphenyl-2-butyn-1,4-dione/1-decyn-3-one;
4,7-undecadiyn-6-one/1-decyn-3-one;
1-(2-furyl)-2-octyn-1-one/1-phenyl-2-propyn-1-one;
1-(2-furyl)-3-phenyl-2-propyn-1-one/1-phenyl-2-propyn-1-one;
1-octyn-3-one/1-phenyl-2-propyn-1-one;
1-(p-tolyl)-2-butyn-1-one/1-phenyl-2-propyn-1-one;
2,5-heptadiyn-4-one/1-phenyl-2-propyn-1-one;
1-(p-methoxyphenyl)-2-propyn-1-one/1-phenyl-2-propyn-1-one;
1,4-diphenyl-2-butyn-1,4-dione/1-phenyl-2-propyn-1-one;
4,7-undecadiyn-6-one/1-phenyl-2-propyn-1-one;
1-(2-furyl)-3-phenyl-2-propyn-1-one/1-(2-furyl)-2-octyn-1-one;
1-octyn-3-one/1-(2-furyl)-2-octyn-1-one   1-(p-tolyl)-2-butyn-1-one;
2,5-heptadiyn-4-one/1-(2-furyl)-2-octyn-1-one;
1-(p-methoxyphenyl)-2-propyn-1-one/1-(2-furyl)-2-octyn-1-one
1,4-diphenyl-2-butyn-1,4-dione/1-(2-furyl)-2-octyn-1-one;
4,7-undecadiyn-6-one/1-(2-furyl)-2-octyn-1-one;
1-octyn-3-one/1-(2-furyl)-3-phenyl-2-propyn-1-one;
1-(p-tolyl)-2-butyn-1-one/1-(2-furyl)-3-phenyl-2-propyn-1-one;

2,5-heptadiyn-4-one/1-(2-furyl)-3-phenyl-2-propyn-1-one;
1-(p-methoxyphenyl)-2-propyn-1-one/1-(2-furyl)-3-phenyl-2-propyn-1-one;
1,4-diphenyl-2-butyn-1,4-dione/1-(2-furyl)-3-phenyl-2-propyn-1-one;
4,7-undecadiyn-6-one/1-(2-furyl)-3-phenyl-2-propyn-1-one;
1-(p-tolyl)-2-butyn-1-one/1-octyn-3-one;
2,5-heptadiyn-4-one/1-octyn-3-one;
1-(p-methoxyphenyl)-2-propyn-1-one/1-octyn-3-one;
1,4-diphenyl-2-butyn-1,4-dione/1-octyn-3-one;
4,7-undecadiyn-6-one/1-octyn-3-one;
2,5-heptadiyn-4-one/1-(p-tolyl)-2-butyn-1-one;
1-(p-methoxyphenyl)-2-propyn-1-one/1-(p-tolyl)-2-butyn-1-one;
1,4-diphenyl-2-butyn-1,4-dione/1-(p-tolyl)-2-butyn-1-one;
4,7-undecadiyn-6-one/1-(p-tolyl)-2-butyn-1-one;
1-(p-methoxyphenyl)-2-propyn-1-one/2,5-heptadiyn-4-one;
1,4-diphenyl-2-butyn-1,4-dione/2,5-heptadiyn-4-one;
4,7-undecadiyn-6-one/2,5-heptadiyn-4-one;
1,4-diphenyl-2-butyn-1,4-dione/1-(p-methoxyphenyl)-2-propyn-1-one;
4,7-undecadiyn-6-one/1-(p-methoxyphenyl)-2-propyn-1-one; and
4,7-undecadiyn-6-one/1,4-diphenyl-2-butyn-1,4-dione.

4. The method of claim 1, wherein the compound of formula 1 is in the composition in a quantity comprised between 0.1% and 40%, of the total volume of the composition.

5. The method of claim 1, wherein said composition further comprises at least one aldehyde selected from the group consisting of the acyclic and non-terpenic aliphatic aldehydes, the non-terpenic alicyclic aldehydes, the terpenic aldehydes, the aliphatic aldehydes substituted by an aromatic group, the bifunctional aldehydes, the aldehydes possessing a non-aromatic unsaturation borne by the carbon in the alpha position of the aldehyde function, the aldehydes possessing an unsaturation in the alpha position of the aldehyde function conjugated with an aromatic ring and the aldehydes the function of which is borne by an aromatic ring.

6. The method of claim 5, wherein said composition comprises a quantity of the aldehyde comprised between 0.5% and 50% of the total volume of the composition.

7. The method of claim 4, wherein the compound of formula 1 is in the composition in a quantity comprised between 0.1% and 10%, of the total weight of the composition.

8. The method of claim 7, wherein said first aldehyde and said second aldehyde are in proportions relative to each other in proportions from 80/20 to 20/80 (V/V) and in a total quantity of aldehydes comprised between 1% and 90% of the total volume of the composition.

9. The method of claim 2, wherein the compound of formula 1 is a pair of compounds of formula 1 selected from the group consisting of the pairs
1-phenyl-2-propyn-1-one/1-decyn-3-one;
1-(2-furyl)-2-octyn-1-one/1-decyn-3-one;
1-(2-furyl)-3-phenyl-2-propyn-1-one/1-decyn-3-one;
1-octyn-3-one/1-decyn-3-one;
1-(p-tolyl)-2-butyn-1-one/1-decyn-3-one;
2,5-heptadiyn-4-one/1-decyn-3-one;
1-(p-methoxyphenyl)-2-propyn-1-one/1-decyn-3-one;
1,4-diphenyl-2-butyn-1,4-dione/1-decyn-3-one;
4,7-undecadiyn-6-one/1-decyn-3-one;
1-(2-furyl)-2-octyn-1-one/1-phenyl-2-propyn-1-one;
1-(2-furyl)-3-phenyl-2-propyn-1-one/1-phenyl-2-propyn-1-one;
1-octyn-3-one/1-phenyl-2-propyn-1-one;
1-(p-tolyl)-2-butyn-1-one/1-phenyl-2-propyn-1-one;
2,5-heptadiyn-4-one/1-phenyl-2-propyn-1-one;
1-(p-methoxyphenyl)-2-propyn-1-one/1-phenyl-2-propyn-1-one;
1,4-diphenyl-2-butyn-1,4-dione/1-phenyl-2-propyn-1-one;
4,7-undecadiyn-6-one/1-phenyl-2-propyn-1-one;
1-(2-furyl)-3-phenyl-2-propyn-1-one/1-(2-furyl)-2-octyn-1-one;
1-octyn-3-one/1-(2-furyl)-2-octyn-1-one 1-(p-tolyl)-2-butyn-1-one;
2,5-heptadiyn-4-one/1-(2-furyl)-2-octyn-1-one;
1-(p-methoxyphenyl)-2-propyn-1-one/1-(2-furyl)-2-octyn-1-one 1,4-diphenyl-2-butyn-1,4-dione/1-(2-furyl)-2-octyn-1-one;
4,7-undecadiyn-6-one/1-(2-furyl)-2-octyn-1-one;
1-octyn-3-one/1-(2-furyl)-3-phenyl-2-propyn-1-one;
1-(p-tolyl)-2-butyn-1-one/1-(2-furyl)-3-phenyl-2-propyn-1-one;
2,5-heptadiyn-4-one/1-(2-furyl)-3-phenyl-2-propyn-1-one;
1-(p-methoxyphenyl)-2-propyn-1-one/1-(2-furyl)-3-phenyl-2-propyn-1-one;
1,4-diphenyl-2-butyn-1,4-dione/1-(2-furyl)-3-phenyl-2-propyn-1-one;
4,7-undecadiyn-6-one/1-(2-furyl)-3-phenyl-2-propyn-1-one;
1-(p-tolyl)-2-butyn-1-one/1-octyn-3-one;
2,5-heptadiyn-4-one/1-octyn-3-one;
1-(p-methoxyphenyl)-2-propyn-1-one/1-octyn-3-one;
1,4-diphenyl-2-butyn-1,4-dione/1-octyn-3-one;
4,7-undecadiyn-6-one/1-octyn-3-one;
2,5-heptadiyn-4-one/1-(p-tolyl)-2-butyn-1-one;
1-(p-methoxyphenyl)-2-propyn-1-one/1-(p-tolyl)-2-butyn-1-one;
1,4-diphenyl-2-butyn-1,4-dione/1-(p-tolyl)-2-butyn-1-one;
4,7-undecadiyn-6-one/1-(p-tolyl)-2-butyn-1-one;
1-(p-methoxyphenyl)-2-propyn-1-one/2,5-heptadiyn-4-one;
1,4-diphenyl-2-butyn-1,4-dione/2,5-heptadiyn-4-one;
4,7-undecadiyn-6-one/2,5-heptadiyn-4-one;
1,4-diphenyl-2-butyn-1,4-dione/1-(p-methoxyphenyl)-2-propyn-1-one;
4,7-undecadiyn-6-one/1-(p-methoxyphenyl)-2-propyn-1-one; and
4,7-undecadiyn-6-one/1,4-diphenyl-2-butyn-1,4-dione.

10. The method of claim 8, wherein the aldehydes of said first and second aldehydes are in proportions of 50/50 (V/V) relative to each other.

11. The method of claim 10, wherein the total quantity of aldehydes is comprised between 10% and 30% of the total volume of the composition.

12. The method of claim 8, wherein the total quantity of aldehydes is comprised between 10% and 30% of the total volume of the composition.

13. The method of claim 1, wherein R and R1 represent, independently or simultaneously, an alkyl chain comprising from 3 to 7 carbon atoms, linear or branched, substituted or unsubstituted.

14. The method of claim 1, wherein R and R1 represent, independently or simultaneously, a cycloalkane comprising from 5 or 6 carbon atoms, substituted or unsubstituted.

15. The method of claim 1, wherein A represents a group selected from the group consisting of —(CH$_2$)x with x representing an integer with a value from 0 to 4.

16. The method of claim 1, wherein A represents a group selected from the group consisting of —(CH$_2$)x with y and z representing, simultaneously or independently, an integer with a value from 0 to 4.

17. The method of claim 5, wherein said composition is a deodorant composition comprising a mixture of at least one first aldehyde (aldehyde of class A) selected from the group consisting of the acyclic and non-terpenic aliphatic aldehydes, the non-terpenic alicyclic aldehydes, the terpenic aldehydes, the aliphatic aldehydes substituted by an aromatic group and the bifunctional aldehydes and at least one second aldehyde (aldehyde of class B) selected from the group consisting of the aldehydes possessing a non-aromatic unsaturation borne by the carbon in the alpha position of the aldehyde function, the aldehydes possessing an unsaturation in the alpha position of the aldehyde function conjugated with an aromatic ring and the aldehydes the function of which is borne by an aromatic ring.

18. The method of claim 6, wherein said composition comprises a quantity of the aldehyde comprised between 1% and 20% of the total weight of the composition.

* * * * *